Sept. 27, 1960 H. M. TIRET Plant Pat. 1,972
FUCHSIA PLANT
Filed Oct. 26, 1959
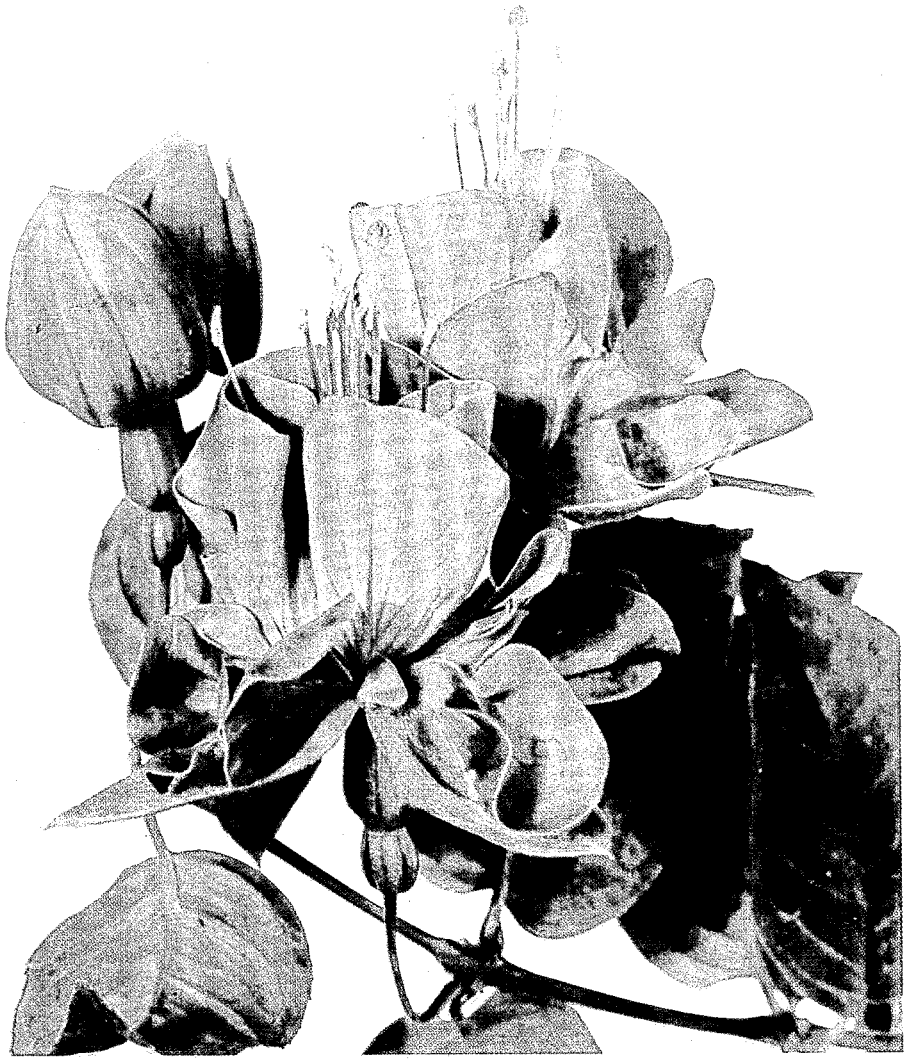

United States Patent Office

Plant Pat. 1,972
Patented Sept. 27, 1960

1,972

FUCHSIA PLANT

Horace M. Tiret, 2126 Taraval St.,
San Francisco 16, Calif.

Filed Oct. 26, 1959, Ser. No. 848,882

1 Claim. (Cl. 47—60)

This invention relates to a new and improved fuchsia plant the principal new and different characteristics of which are the size and color of the flowers combined with excellent form and trailing habit of growth.

The accompanying color drawing illustrates the plant in bloom and the aforementioned new and different characteristics.

The plant was derived as a hybrid from seedling (unpatented) not introduced to the trade, namely 9/21/1 and Georgana (Plant Patent Number 1,501) the figures representing applicant's own breeding symbols. The plant has been asexually reproduced at Colma, California, by cuttings which retained the characteristics of the parent fuschsia.

The plant is a trailer and grows vigorously. It is very self-branching with medium foliage and large double heliotrope colored flowers. The flowers are produced in abundance. It is an early bloomer.

In the accompanying drawing, the figure shows a typical branch tip, the drawing representing approximate actual size.

A detailed description of this new variety of fuchsia plant follows:

*Habit of growth.*—Vigorous, trailing variety. Blooms early.

*Foliage.*—Medium in size, medium green in color. Leaves are lightly veined with edges slightly serrated.

Branches are reddish-brown. The mature leaf is approximately 2⅛″ in length and 1½″ in width at the widest point.

*Petals.*—The petals are flushed crimson near the base, otherwise heliotrope (British Horticultural Chart #636) which is the predominant color. When the flower first opens the petals are the same color.

The petals number approximately 29, the outer petals flaring out horizontally from the four center petals. The diameter of the mature flower is approximately 3¼″. Length of the large petals is 1¾″, with 1¾″ (spread out). Appearance of the petals is smooth.

*Ovary.*—Brownish green in color. Length ½″. Width at widest point 5/16″, when flower is fully open.

*Tube.*—Medium—long and slender. Length is approximately 15/16″. Width at widest point 5/16″. Crimson in color (British Horticultural Chart #22).

*Sepals.*—Topside and underside are approximately the same color which is crimson. Sepals are broad and long and recurved toward the tube. Some of the sepals recurve horizontally. They are four in number, 2″ in length and ¾″ in width, at widest point. Outerside, smooth and satiny. Underside, smooth and velvety.

*Stamens.*—Eight in number, colored crimson, with flesh colored anthers. Slender, length 2¼″ mature flower.

*Pistil.*—The style is approximately 2½″ in length and 1/32″ in width. It is crimson in color and the stigma is also crimson.

*Buds.*—Crimson in color. Length from ovary is approximately 2¼″, and width at widest point 1″.

*Parentage.*—Applicant's own seedling, 9/21/1 (unpatented) not introduced to the trade, and Georgana (patented), the figures representing applicant's own breeding symbols.

Having thus disclosed by discovery, I claim:

A new and different fuchsia plant herein described, characterized by the size and heliotrope color of the flowers combined with excellent form and trailing habit of growth.

No references cited.